United States Patent [19]

Kurumada et al.

[11] Patent Number: 5,730,939
[45] Date of Patent: Mar. 24, 1998

[54] AUTOMATIC ANALYZER HAVING FLUID ABNORMALITIES DETECTION DEVICE

[75] Inventors: Rumi Kurumada; Atsushi Takahashi, both of Hitachinaka; Tomonori Mimura, Tomobe-machi, all of Japan

[73] Assignee: Hitachi, Ltd., Tokyo, Japan

[21] Appl. No.: 610,183

[22] Filed: Mar. 4, 1996

[30] Foreign Application Priority Data

Mar. 17, 1995 [JP] Japan ........................ 7-059375

[51] Int. Cl.$^6$ ........................................ G01N 37/00
[52] U.S. Cl. ........................ 422/67; 422/64; 436/50
[58] Field of Search ............................ 422/63, 64, 67, 422/68.1; 436/43, 47, 49, 50, 55; 364/496, 497, 499

[56] References Cited

U.S. PATENT DOCUMENTS

| | | | |
|---|---|---|---|
| 4,451,433 | 5/1984 | Yamashita et al. | 422/63 |
| 4,539,296 | 9/1985 | Manabe | 436/47 |
| 4,612,289 | 9/1986 | Futura et al. | 436/34 |
| 4,678,755 | 7/1987 | Shinohara et al. | 436/43 |
| 4,939,095 | 7/1990 | Yokotani | 436/47 |
| 4,971,913 | 11/1990 | Manabe et al. | 436/55 |
| 5,051,238 | 9/1991 | Umetsu et al. | 422/64 |
| 5,100,622 | 3/1992 | Mimura et al. | 422/67 |
| 5,154,311 | 10/1992 | Ushikubo | 422/81 |
| 5,324,635 | 6/1994 | Kawase et al. | 435/7.94 |
| 5,424,212 | 6/1995 | Pinsi-Ober et al. | 436/50 |
| 5,473,551 | 12/1995 | Sato et al. | 364/496 |

*Primary Examiner*—Long V. Le
*Attorney, Agent, or Firm*—Fay, Sharpe, Beall, Fagan, Minnich & McKee

[57] ABSTRACT

An automatic analyzer in which abnormalities of reagents and samples used are displayed. Abnormalities are displayed in the form of a list which is composed of an alarm colored display table and an alarm detailed table. With respect to the alarm colored display, alarms which have occurred in reagents, standard solutions and control analytes in each analytic item are displayed in the form of a list so as to be classified by colors. With respect to the alarm detailed table, analytic information concerning abnormality of reagent, abnormality of standard solution, abnormality of control analyte, number of analyses, term of validity, alarm, etc. and information concerning the kind of reagent, the kind of standard solution, the kind of control analyte, the setting position, etc. which will be newly required for analysis in the future now are displayed.

15 Claims, 6 Drawing Sheets

FIG. 1

| ITEM NAME | REAGENT | STANDARD SOLUTION | CONTROL |
|---|---|---|---|
| ITEM 20 | ▨ | | |
| ITEM 2 | ▨ | | |
| ITEM 5 | ▨ | | |
| ITEM 6 | | ▨ | |
| ITEM 10 | ▨ | | |
| ITEM 18 | ▨ | | |
| ITEM 7 | ▨ | | |
| ITEM 11 | | ▨ | |
| ITEM 19 | | ▨ | |
| ITEM 21 | | | ▨ |
| ITEM 25 | | | ▨ |

<REAGENT>

| LEVEL | ITEM NAME | REAGENT KIND | POSITION | PRODUCTION NUMBER | ALARM DETAIL |
|---|---|---|---|---|---|
| ▨ | ITEM 20 | REAGENT 1 | 2-40 | 150 | NO SETTING (DISK 1) |
| ▨ | ITEM 20 | REAGENT 4 | 1-10 | 100 | SETTING POSITION ERROR (DISK 1) |
| ▨ | ITEM 2 | REAGENT 1 | | | NO AMOUNT OF RESIDUE |
| ▨ | ITEM 5 | REAGENT 3 | 2-32 | 124 | SMALLER AMOUNT OF RESIDUE (LESS THAN 100 TESTS' AMOUNT) |
| ▨ | ITEM 10 | REAGENT 1 | 1-5 | 130 | OVER THE NUMBER OF DAYS OF USE |
| ▨ | ITEM 18 | REAGENT 1 | 1-3 | 129 | EXPIRATION OF VALID TERM |
| ▨ | ITEM 7 | REAGENT 3 | 2-15 | 524 | SMALLER AMOUNT OF RESIDUE THAN THE ONE DAY'S AMOUNT (THAN 400 TESTS' AMOUNT) |

<STANDARD SOLUTION>

| LEVEL | STANDARD SOLUTION NAME | POSITION | PRODUCTION NUMBER | ALARM DETAIL | NUMBER OF RESIDUAL ANALYSES |
|---|---|---|---|---|---|
| ▨ | STANDARD SOLUTION 0 | 55 | 10039 | NO SETTING (Pos. 1-50) | 130 |
| ▨ | STANDARD SOLUTION 2 | 12 | 10050 | SETTING POSITION ERROR (Pos. 1-50) | 0 |
| ▨ | STANDARD SOLUTION 1 | 15 | 10029 | STANDARD SOLUTION SHORTAGE | 80 |
| ▨ | STANDARD SOLUTION 3 | 47 | 10012 | WITH DATA ALARM | 120 |
| ▨ | STANDARD SOLUTION 9 | | 10043 | EXPIRATION OF VALID TERM | 120 |

<CONTROL ANALYTE>

| LEVEL | CONTROL NAME | POSITION | PRODUCTION NUMBER | ALARM DETAIL |
|---|---|---|---|---|
| ▨ | CONTROL 1 | 10 | 10039 | CONTROL ANALYTE SHORTAGE |
| ▨ | CONTROL 3 | 18 | 10012 | WITH DATA ALARM |
| ▨ | CONTROL 9 | 7 | 10043 | EXPIRATION OF VALID TERM |

ALARM REPORT

<REAGENT>

| ITEM NAME | REAGENT KIND | POSITION | PRODUCTION NUMBER | ALARM DETAIL | NUMBER OF RESIDUAL ANALYSIS |
|---|---|---|---|---|---|
| ITEM 20 | REAGENT 1 | 2-40 | 150 | NO SETTING (DISK 1) | |
| ITEM 20 | REAGENT 4 | 1-10 | 100 | SETTING POSITION ERROR (DISK 1) | 130 |
| ITEM 2 | REAGENT 1 | | | NO AMOUNT OF RESIDUE | 0 |
| ITEM 5 | REAGENT 3 | 2-32 | 124 | SMALLER AMOUNT OF RESIDUE (LESS THAN 100 TESTS' AMOUNT) | 80 |
| ITEM 10 | REAGENT 1 | 1-5 | 130 | OVER THE NUMBER OF DAYS OF USE | 120 |
| ITEM 18 | REAGENT 1 | 1-3 | 129 | EXPIRATION OF VALID TERM | 120 |
| ITEM 7 | REAGENT 3 | 2-15 | 524 | SMALLER AMOUNT OF RESIDUE THAN ONE DAY'S AMOUNT (THAN 400 TESTS' AMOUNT) | 390 |

<STANDARD SOLUTION>

| STANDARD SOLUTION NAME | POSITION | PRODUCTION NUMBER | ALARM DETAIL |
|---|---|---|---|
| STANDARD SOLUTION 0 | | 10039 | NO SETTING (Pos. 1-50) |
| STANDARD SOLUTION 2 | 55 | 10050 | SETTING POSITION ERROR (Pos. 1-50) |
| STANDARD SOLUTION 1 | 12 | 10029 | STANDARD SOLUTION SHORTAGE |
| STANDARD SOLUTION 3 | 15 | 10012 | WITH DATA ALARM |
| STANDARD SOLUTION 9 | 47 | 10043 | EXPIRATION OF VALID TERM |

<CONTROL ANALYTE>

| CONTROL NAME | POSITION | PRODUCTION NUMBER | ALARM DETAIL |
|---|---|---|---|
| CONTROL 1 | 10 | 10039 | CONTROL ANALYTE SHORTAGE |
| CONTROL 3 | 18 | 10012 | WITH DATA ALARM |
| CONTROL 9 | 7 | 10043 | EXPIRATION OF VALID TERM |

AUTOMATIC ANALYZER HAVING FLUID ABNORMALITIES DETECTION DEVICE

BACKGROUND OF THE INVENTION

The present invention relates to an automatic analyzer and particularly relates to an automatic analyzer in which abnormalities of reagents and samples used are displayed.

In an ordinary automatic analyzer, not only the setting states of reagents, control analytes, standard solutions, and so on, alarms, analytic result data, etc. are displayed on separate scenes but also such display information is displayed whether it is abnormal or not.

Further, prediction of abnormality of analysis and display of alarms in the future of several hours from now are insufficient but merely the period required for exchanging parts can be displayed.

In the automatic analyzer, reagents, control analytes, standard solutions, etc. need be operated in combination so that analytic result data are obtained by using the reagents, the control analytes, the standard solutions, etc. In the automatic analyzer using the aforementioned ordinary technique, it is however difficult that all items are managed by a human being because these matters have different parameters and different terms of validity.

Further, in the aforementioned ordinary technique, it is not easy to predict the abnormality of analysis in the future of several hours from now. Accordingly, there arises a problem in that re-analyzing or the like is required to thereby prevent speedy analysis and saving of reagents, control analytes and standard solutions because a measure counter to abnormality must be taken after the occurrence of data failure.

SUMMARY OF THE INVENTION

An object of the present invention is to provide an automatic analyzer adapted to make it possible to take speedy measures against abnormality.

Another object of the present invention is to provide an automatic analyzer adapted to make it possible to save reagents against abnormality.

An additional object of the present invention is to provide an automatic analyzer adapted to make it possible to save reagents and samples against abnormality.

A yet another object of the present invention is to provide an automatic analyzer adapted to make it possible to lighten the lowering of analytic accuracy caused by the occurrence of abnormality.

According to an aspect of the present invention, an automatic analyzer is provided which comprises means for reacting samples with reagents so as to obtain reacted solutions, means for measuring the reacted solutions so as to analyze analytic items in the samples, means for detecting possible abnormalities of the reagents, and means for displaying the abnormalities in list form with the abnormalities associated with the analytic items.

In the above automatic analyzer, preferably, the displaying means displays the abnormalities with the same ranked on the basis of a predetermined standard.

In the above automatic analyzer, preferably, the predetermined standard is based on degree of significance of the abnormalities.

In the above automatic analyzer, preferably, the predetermined standard is based on degree of emergence for measures against the abnormalities.

In the above automatic analyzer, preferably, the displaying means displays the ranked abnormalities with the same differently colored.

In the above automatic analyzer, preferably, the displaying means displays the abnormalities in the order ranked.

According to another aspect of the present invention, an automatic analyzer is provided which comprises means for reacting samples with reagents so as to obtain reacted solutions, means for measuring the reacted solutions so as to analyze analytic items in the samples, means for detecting possible abnormalities of the samples and the samples, and means for displaying the abnormalities in the form of a list, the list comprising a schematic list indicating relationships between the detected abnormalities and the analytic items for the samples and the reagents, and a detailed list indicating details of the abnormalities corresponding to the relationships between the abnormalities and the analytic items for the samples and the reagents.

According to an additional aspect of the present invention, an automatic analyzer is provided which comprises means for reacting samples with reagents so as to obtain reacted solutions, means for measuring the reacted solutions so as to analyze analytic items in the samples, means for predictively detecting possible abnormalities of the samples in a predetermined time, and means for displaying the abnormalities in the form of a list with the abnormalities associated with the analytic items.

In the above automatic analyzer according to the additional aspect of the present invention, preferably, the displaying means displays the abnormalities with the same ranked on the basis of a predetermined standard.

In the above automatic analyzer according to the additional aspect of the present invention, preferably, the displaying means displays the ranked abnormalities in the order ranked.

According to a further aspect of the present invention, an automatic analyzer is provided which comprises means for reacting samples with reagents so as to obtain reacted solutions, means for measuring the reacted solutions so as to analyze analytic items in the samples, means for predictively detecting possible abnormalities of the samples and the reagents in a predetermined time, and means for displaying the abnormalities in the form of a list with the abnormalities associated with the analytic items, the list comprising a schematic list indicating relationships between the detected abnormalities and the analytic items for the samples and the reagents, and a detailed list indicating details of the abnormalities corresponding to the relationships between the abnormalities and the analytic items for the samples and the reagents.

According to a further additional aspect of the present invention, an automatic analyzer is provided which comprises means for reacting standard solutions and control samples with reagents, respectively, so as to obtain reacted solutions, means for measuring absorbance of the reacted solutions so as to analyze analytic items in the standard solutions and the control samples, means for detecting possible abnormalities of the standard solutions, the control samples and the reagents in a predetermined time, and means for displaying the abnormalities in the form of a list with the abnormalities of the reagents associated with the analytic items.

In the above automatic analyzer according to the further additional aspect of the present invention, preferably, the list comprises a schematic list indicating relationships between the detected abnormalities and the analytic items for the standard solutions, the control samples and the reagents, and a detailed list indicating details of the abnormalities corresponding to the relationships between the abnormalities and the analytic items for the standard solutions, the control samples and the reagents.

In the above automatic analyzer according to the further additional aspect of the present invention, preferably, the details of the abnormalities include information concerning kind, setting position, presence or absence, residual amount and allowed time of the reagents.

In the above automatic analyzer according to the further additional aspect of the present invention, preferably, the details of the abnormalities include information concerning name, setting position, presence or absence, residual amount, data failure and allowed time of the standard solutions and the control samples.

Other objects and features of the present invention will become apparent from the descriptions of preferred embodiments of the present invention taken in connection with the accompanying drawings.

DESCRIPTION OF THE PREFERRED EMBODIMENTS

Figure 1:
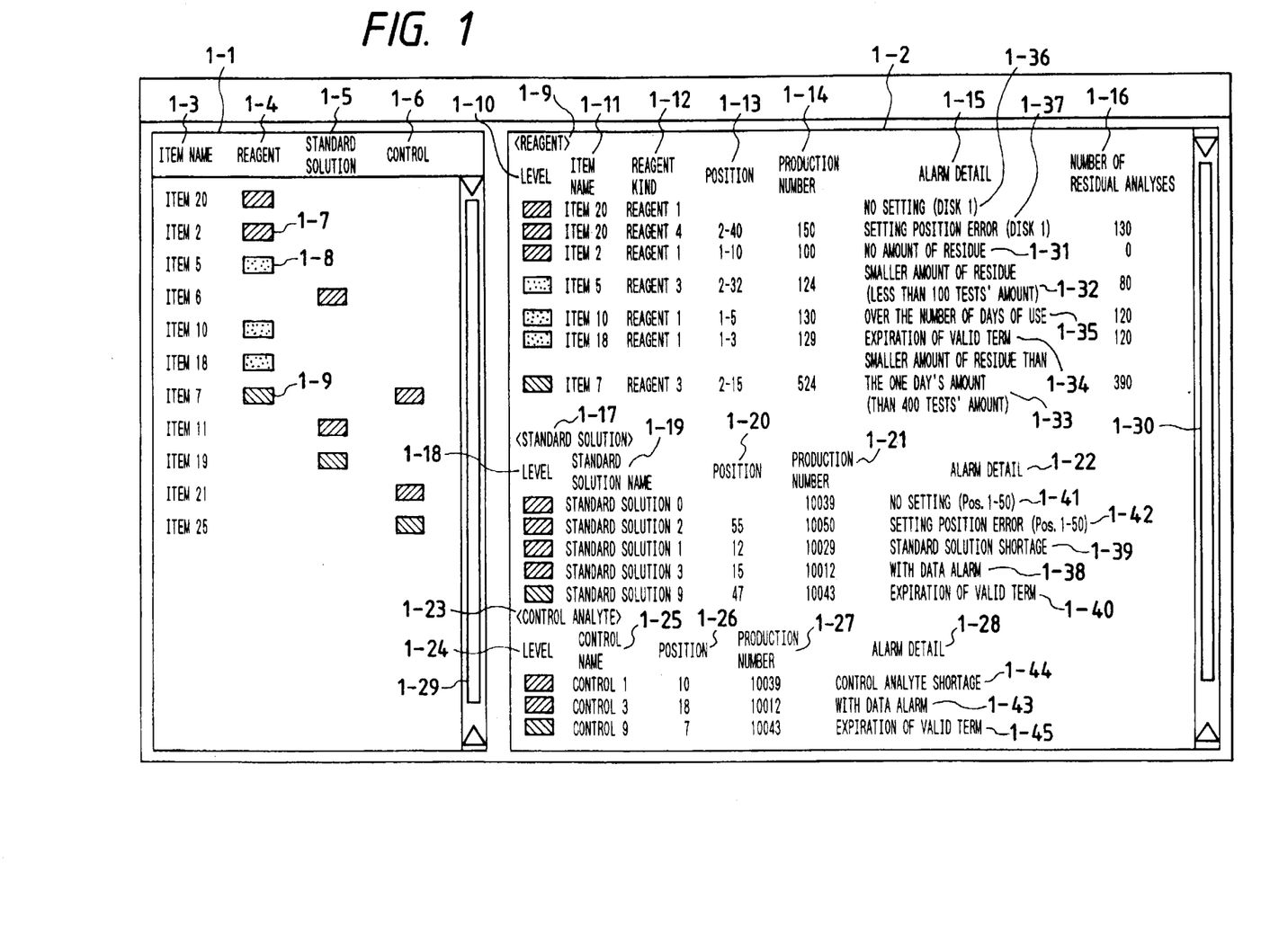
FIG. 1 is a view showing an example of an alarm list display according to the present invention.

In advance of the detailed description of an embodiment of the present invention, the outline of a preferred embodiment of the present invention will be described with reference to FIG. 1. FIG. 1 shows an example of display of functions in accordance with the present invention, which is composed of an alarm colored display table 1-1, and an alarm detailed table 1-2. The alarm colored display table 1-1 is a table for displaying abnormality in brief. Alarms which have occurred in reagents, standard solutions and control analytes in respective analytic items are listed on the alarm colored display table 1-1 so as to be classified by colors. Analytic information concerning the abnormality of reagents, the abnormality of standard solutions, the abnormality of control analytes, the number of analyses, the term of validity, alarms, etc. and information concerning the kinds, set positions, or the like, of reagents, standard solutions and control analytes which will be newly required for analysis several hours in the future are listed on the alarm detailed table 1-2.

The alarm colored display table 1-1 will be described first. The names of items in which alarms have occurred in reagents, standard solutions and control analytes are displayed in the column 1-3. Colors showing the levels of alarms are displayed in corresponding columns of reagent 1-4, standard solution 1-5 and control analyte 1-6 in corresponding lines of items in which alarms have occurred. The "colors showing the levels of alarms" expresses the degree of alarm significance or the degree of countermeasure emergency so that red indicates an alarm in the level of emergency, yellow indicates an alarm in the level of caution, and purple indicates an alarm in the level of warning. For example, 1-7 is red which indicates the fact that a red-level alarm has occurred in the reagent of item 2. For example, 1-8 is yellow which indicates the fact that a yellow-level alarm has occurred in the reagent of item 5. For example, 1-9 is purple which indicates the fact that a purple-level alarm has occurred in the reagent of item 7. When a plurality of alarms have occurred in one item, the highest alarm in the degree of significance is displayed preferentially. Similarly, alarm colors displayed in the standard solution column and in the control analyte column express level alarms in respective items. Further, items in which alarms have occurred in reagents, standard solutions and control analytes are arranged in the column of item name 1-3 in order of alarm significance. That is, of items displayed on the alarm colored display table 1-1, the upper item requires a more urgent countermeasure than the lower item. Whenever an alarm occurs, the table is real-time edited and displayed again.

The alarm detailed table 1-2 will be described below. Information necessary for the alarm contents and alarm countermeasures displayed on the alarm colored table 1-1 with respect to reagents, standard solutions and control analytes is displayed on the alarm detailed table 1-2.

The reference numeral 1-9 designates an alarm detailed display section for reagents (including cleaning solutions, sample diluents, and so on). Alarm level colored display 1-10, item name 1-11, kind of reagent 11-2, reagent set position 1-13, reagent production number 1-14, alarm detail 1-15 and number of residual analyses 1-16 are displayed on the alarm detailed display section 1-9.

When a plurality of alarms have occurred in one item, all alarms are displayed in this portion. Alarms concerning the abnormality of reagent and the number of analyses are (1) no amount of residue 1-31, (2) smaller amount of residue (than the 100 tests' amount) 1-32, (3) smaller amount of residue than the one day's amount 1-33, etc. Alarms concerning the expiration of the term of validity are (4) expiration of the term of validity of reagent 1-34, (5) over the number of days of use 1-35 from the start day of use (unsealed day), etc. Alarms concerning reagents which will be newly required for analysis in the future of several hours from now are (6) no setting of reagents in items requested to be analyzed 1-36, (7) setting position error 1-37, etc. In the case where setting positions or setting disks are determined as the positions where reagents are set, the positions or disk numbers are, respectively, displayed in the alarm detail column 1-15. The examples of the aforementioned reagent alarms (1) to (7) occur before analysis or in the period of analysis.

Alarm level colored display 1-18, standard solution name 1-19, position 1-20, production number 1-21 and alarm detail 1-22 are displayed on a standard solution alarm detailed display section 1-17. Alarms concerning the abnormality of standard solutions and the number of analyses are (1) data alarm 1-38, (2) standard solution shortage alarm (no amount of residue) 1-39, etc. Alarms concerning the expiration of the term of validity are (3) expiration of the term of validity of standard solution 1-40, etc. Alarms concerning standard solutions which will be newly required for analysis in the future of several hours from now are (4) no setting of standard solutions in items requested to be analyzed 1-41, (5) setting position error 1-42, etc. Positions to which standard solutions need be set are displayed in the alarm detail column 1-22. The examples of the aforementioned standard solution alarms (1) and (2) occur only in the period of analysis. The examples of the standard solution alarms (3) to (5) occur before analysis or in the period of analysis.

Alarm level colored display 1-24, control analyte name 1-25, position 1-26, production number 1-27 and alarm detail 1-28 are displayed on a control analyte alarm detailed display section 1-23. Alarms concerning the abnormality of control analytes and the number of analyses are (1) data alarm 1-43, (2) control analyte shortage alarm (no amount of residue) 1-44, etc. Alarms concerning the expiration of the term of validity are (3) expiration of the term of validity of control analyte 1-45, etc. Alarms concerning control analytes which will be newly required for analysis in the future of several hours from now are (4) no setting of control analytes in items requested to be analyzed, (5) setting position error, etc. Positions to which control analytes need be set are displayed in the alarm detail column 1-28. The examples of the aforementioned control analyte alarms (1) and (2) occur only in the period of analysis. The examples of the control analyte alarms (3) to (5) occur before analysis or in the period of analysis.

Further, scroll bars 1-29 and 1-30 are used for scrolling the display page when the number of alarm items is larger than the number of display lines on a screen.

As described above, the alarm colored display table 1-1 makes it easy to grasp items in which alarms have occurred and the significance of the alarms which have occurred. The alarm detailed table 1-2 indicates clearly countermeasures which will be taken.

An embodiment of the present invention will be described below with reference to FIGS. 2 through 6.

Figure 2:
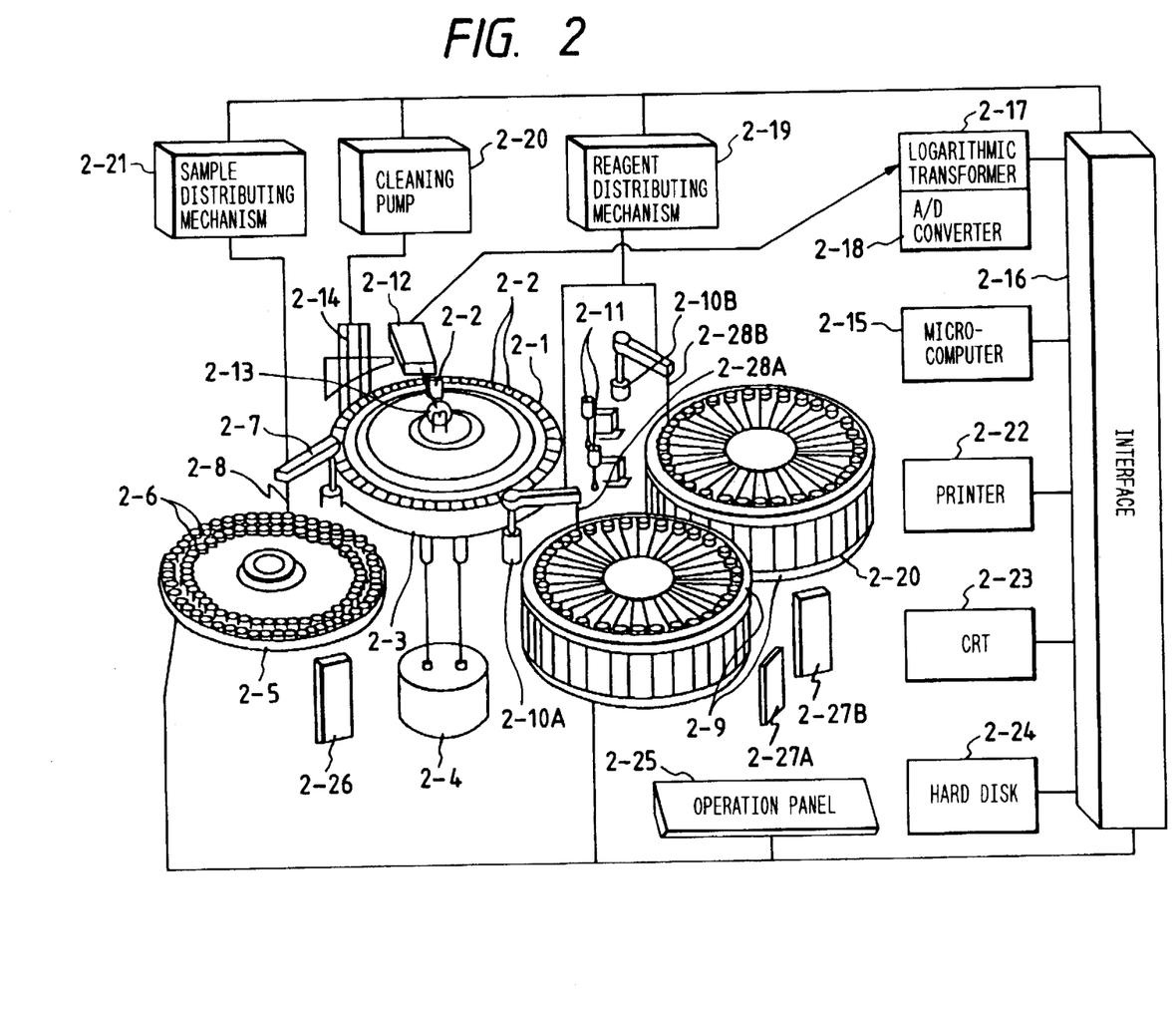
FIG. 2 is a view showing the configuration of an automatic analyzer as an embodiment of the present invention.

FIG. 2 is a view of an apparatus configuration of an automatic analyzer. In FIG. 2, the reference numeral 2-1 designates a reaction disk. Reaction vessels 2-2 are disposed on the outer circumference of the reaction disk 2-1. The temperature of the reaction disk 2-1 as a whole is kept at a predetermined value by a heat retaining tank 2-3. The reference numeral 2-4 designates a heat retaining water supply portion for the heat retaining tank 2-3. The reference numeral 2-5 designates a sample disk mechanism. A large number of sample cups 2-6 are disposed on this mechanism 2-5. The reference numeral 2-26 designates a sample cup bar code reader which decodes bar codes added to the sample cups 2-6. A sample in each sample cup 2-6 is suitably extracted by a nozzle 2-8 of a sample pipetting mechanism 2-7 and injected into a reaction vessel in a sample injection position. The nozzle 2-8 has a liquid surface sensor at its end, so that the amount of the sample residue can be measured by the liquid surface sensor. The reference numeral 2-9 designates reagent disk mechanisms on which reagent cups are disposed. The reagent disk mechanisms 2-9 are provided with reagent pipetting mechanisms 2-10A and 2-10B, respectively. The reference numerals 2-27A and 2-27B designate reagent bottle bar code readers which decode bar codes added to reagent cups. Reagents necessary for analysis are suitably extracted and injected into reaction vessels 2-2 by nozzles 2-28A and 2-28B of the reagent pipetting mechanisms 2-10A and 2-10B. Each of the nozzles 2-28A and 2-28B has a liquid surface sensor at its end, so that the amount of the reagent residue can be measured. The reference numeral 2-11 designates a stirring mechanism. The reference numeral 2-12 designates a multi-wavelength photometer; and 2-13, a light source. A reaction vessel 2-2 for storing an object to be measured is disposed between the multi-wavelength photometer 2-12 and the light source 2-13. The reference numeral 2-14 designates a cleaning mechanism. In a control system and a signal processing system, the reference numeral 2-15 designates a microcomputer; 2-16, an interface; 2-17, a logarithmic transformer; 2-18, an A/D converter; 2-19, a reagent distributing mechanism; 2-20, a cleaning pump; and 2-21, a sample distributing mechanism. Further, the reference numeral 2-22 designates a printer for printing a report; 2-23, a CRT for displaying the report; 2-24, a hard disk as a storage device; and 2-25, an operation panel (keyboard) for inputting data.

The principle of analysis in the aforementioned automatic analyzer will be described below. A predetermined amount of each sample is injected into a reaction vessel 2-2 by using the nozzle 2-8 of the sample pipetting mechanism 2-7 in accordance with analytic parameters stored in a memory in the micro-computer 2-15. Then, the reaction vessel 2-2 containing the sample injected therein is moved to a reagent injection position by rotating the reaction disk 2-1. Then, a predetermined amount of a reagent is injected into the reaction vessel 2-2 having the sample injected by using the nozzles 2-28A and 2-28B of the reagent pipetting mechanisms 2-10A and 2-10B in accordance with analytic parameters stored in the memory in the micro-computer 2-15. Then, the sample and the reagent are stirred by the stirring mechanism 2-11 and mixed. When the reaction vessel 2-2 crosses the photometric position, absorbance is measured by the multi-wavelength photometer 2-12. The absorbance thus measured is fed into the micro-computer 2-15 via the logarithmic transformer 2-17, the A/D converter 2-18 and the interface 2-16. The absorbance is converted into density data on the basis of an analytical curve (calibration) which is generated from the absorbance of a standard solution measured by an analyzing method designated correspondingly to each item in advance. The component density data thus measured is put out to the printer or display.

In the embodiment of the present invention, lists of reagents, standard solutions and control analytes are displayed in accordance with the following judgment rule.
Reagent When items requested to be analyzed satisfy the following seven conditions, the items are displayed as a list. Alarms (1) to (7) occur before analysis or in the period of analysis.

(1) When the number of residual analyses is not larger than the number of scheduled analyses in one day, the alarm level is selected to be purple. The number of scheduled analyses in one day can be set freely by a user. The number of scheduled analyses in one day is inputted through the operation panel by using a certain scene.

(2) When the number of residual analyses is not larger than the number of analyses for the reagent residue shortage alarm, the alarm level is selected to be yellow.

The number of analyses for the reagent residue shortage alarm can be set freely by the user, and this number is inputted through the operation panel by using a certain scene.

(3) When the number of residual analyses is zero, the alarm level is selected to be red.

(4) When the term of validity expires, the alarm level is selected to be yellow.

(5) When the term of use exceeds a predetermined number of days after a day on which the reagent was unsealed, that is, after a day on which the reagent began to be used (a day on which the reagent was set in the reagent disk and on which the bar code was decoded first), the alarm level is selected to be yellow.

(6) When the setting position is mistaken, the alarm level is selected to be yellow.

(7) When there is no reagent in an item requested to be analyzed, the alarm level is selected to be red.

Standard Solution

When standard solutions requested to be analyzed satisfy the following six conditions, the standard solutions are displayed as a list. Alarms (5) and (6) occur in the period of analysis. Alarms (1) to (4) occur before analysis or in the period of analysis.

(1) When a standard solution scheduled to be used for analysis in a period of from 20 minutes to 1 hour is not set in the sample disk mechanism 2-5, the alarm level is selected to be purple.

(2) When a standard solution scheduled to be used for analysis in a period of from 3 minutes to 20 minutes is not set in the sample disk mechanism 2-5, the alarm level is selected to be yellow.

(3) When a standard solution scheduled to be used for analysis in a period of 3 minutes is not set in the sample disk mechanism 2-5, the alarm level is selected to be red.

(4) When the term of validity expires, the alarm level is selected to be yellow.

(5) When a standard solution shortage alarm is given to the analytic data, the alarm level is selected to be red.

(6) When a standard solution abnormality alarm is given to the analytic data, the alarm level is selected to be red.

Control Analyte

When control analytes requested to be analyzed satisfy the following six conditions, the control analytes are displayed as a list. Alarms (5) and (6) occur in the period of analysis. Alarms (1) to (4) occur before analysis or in the period of analysis.

(1) When a control analyte scheduled to be used for analysis in a period of from 20 minutes to 1 hour is not set in the sample disk mechanism 2-5, the alarm level is selected to be purple.

(2) When a control analyte scheduled to be used for analysis in a period of from 3 minutes to 20 minutes is not set in the sample disk mechanism 2-5, the alarm level is selected to be yellow.

(3) When a control analyte scheduled to be used for analysis in a period of 3 minutes is not set in the sample disk mechanism 2-5, the alarm level is selected to be red.

(4) When the term of validity expires, the alarm level is selected to be purple.

(5) When a control analyte shortage alarm is given to the analytic data, the alarm level is selected to be red.

(6) when a control analyte abnormality alarm is given to the analytic data, the alarm level is selected to be red.

Figure 3:
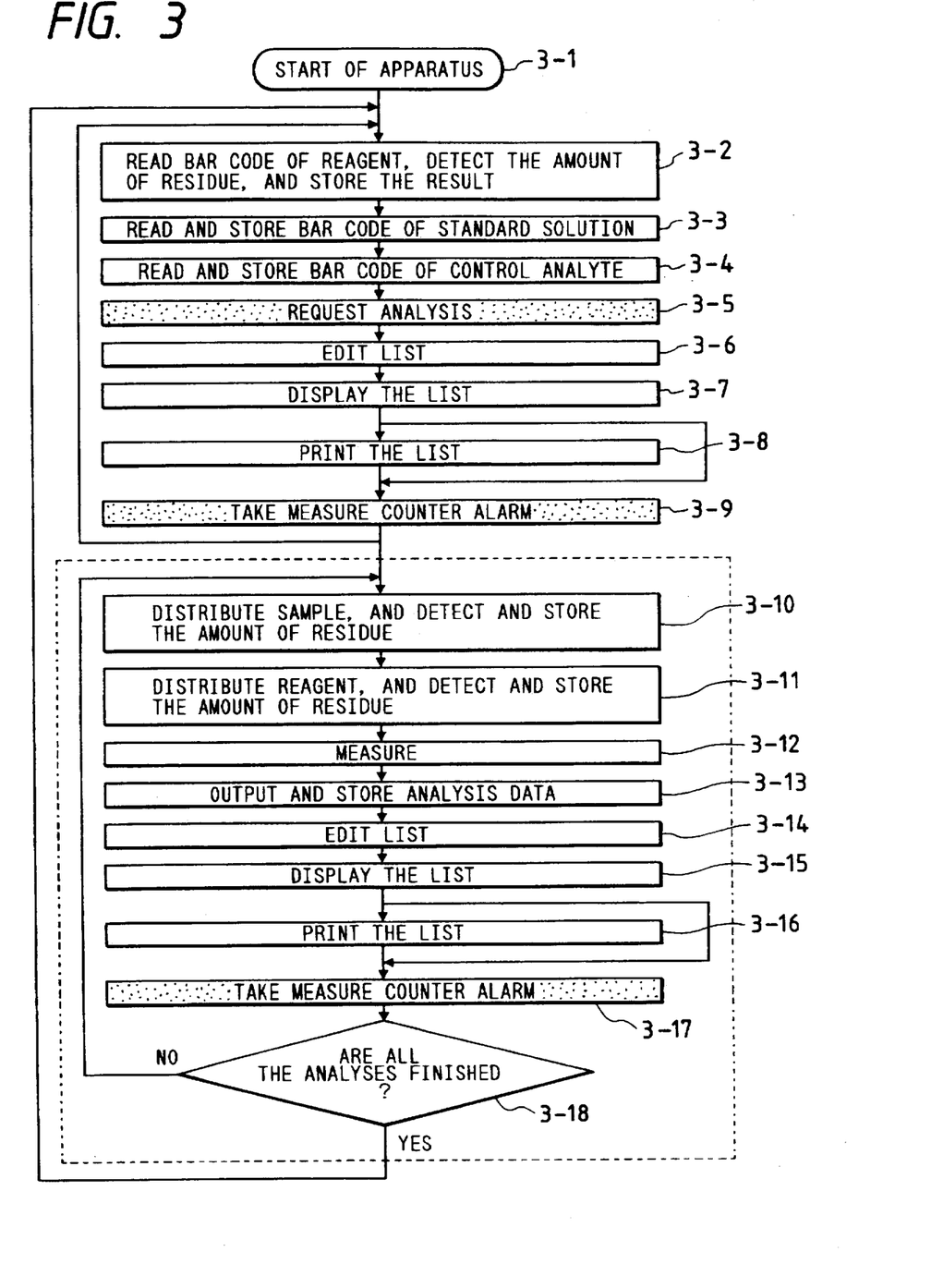
FIG. 3 is a flow chart showing the operation of the automatic analyzer as an embodiment of the present invention.

FIG. 3 is a flow chart showing the routine of displaying the list in the aforementioned manner. In FIG. 3, the steps having a dotted background show steps of user's hand work, and the other steps show steps of automatic analyzer's work. Further, analytic parameters and alarm parameters such as the number of scheduled analyses in one day, the number of analyses for the reagent residue shortage alarm, etc., are set in advance correspondingly to items and stored in the hard disk.

Step 3-1: The automatic analyzer is started up.

Step 3-2: The bar codes of reagents are read so that the amounts of the residues are detected and stored. The operation of the automatic analyzer will be described with reference to FIG. 2. After a bar code label containing information concerning kind of reagent, production number and term of validity is stuck to each reagent cup, the reagent cup is set in the reagent disk mechanism 2-9. The reagent disk mechanism 2-9 rotates, so that the bar code label added to each reagent cup is decoded by the bar code readers 2-27A and 2-27B to thereby grasp the setting position. At the same time, the nozzles 2-28A and 2-28B detect the amounts of the reagents in the reagent cups to thereby measure the amounts of the reagent residues. The information concerning the setting position, the kind of reagent, the production number, and the term of validity, as well as the amounts of the reagent residues are stored in the memory in the micro-computer 2-15.

Step 3-3: The bar codes of standard solutions are read and stored. The operation of the automatic analyzer will be described with reference to FIG. 2. After a bar code label containing information concerning kind of standard solution, production number and term of validity is stuck to each standard solution sample cup, the sample cup is set in the sample disk mechanism 2-5. The sample disk mechanism 2-5 rotates, so that the bar code added to each sample cup 2-6 is decoded by the bar code reader 2-26 to thereby grasp the setting position. The information concerning the setting position, the kind of standard solution, the term of validity, and the production number is stored in the memory in the micro-computer 2-15.

Step 3-4: The bar codes of control analytes are read and stored. The operation of the automatic analyzer will be described with reference to FIG. 2. After a bar code label containing information concerning kind of control analyte, production number and term of validity is stuck to each control analyte sample cup, the sample cup is set in the sample disk mechanism 2-5. Similarly to the case of the standard solution, the sample disk mechanism 2-5 rotates, so that the bar code added to each sample cup 2-6 is decoded by the bar code reader 2-26 to thereby grasp the setting position. The information concerning the setting position, the kind of control analyte, the term of validity, and the production number is stored in the memory in the micro-computer 2-15.

Step 3-5: A request to analyze at least one sample (selected from standard solutions necessary for forming calibration, control analytes used for checking the apparatus state such as probe choking, reagent deterioration, etc. in the measurement of patient analytes, and patient analytes) is inputted by the user through the operation panel by using a corresponding scene.

Step 3-6: Alarm lists are edited on the basis of the information stored by the steps 3-2, 3-3 and 3-4 and the analysis request inputted by the step 3-5.

The routine of editing the alarm lists will be described with reference to FIGS. 4 and 5. As an alarm colored display table, a table for storing alarms of reagents, standard solutions and control analytes by items is provided in the memory in the micro-computer. Similarly, an alarm detailed table on which reagents are classified by items and kinds thereof, standard solutions are classified by kinds thereof and control analytes are classified by kinds thereof is provided in the memory in the micro-computer.

Figure 4:
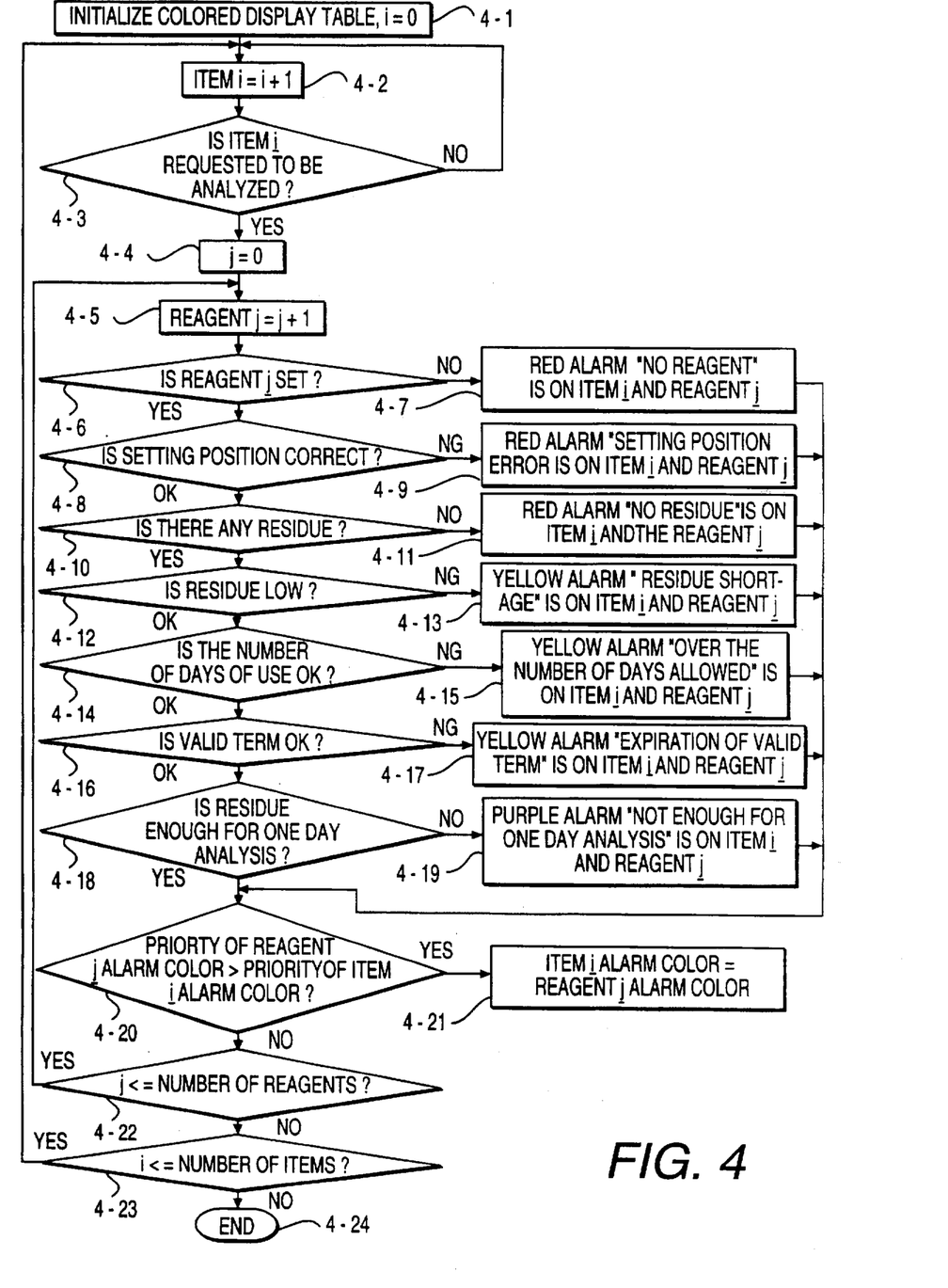
FIG. 4 is a flow chart of the detailed operation showing part of the operation flow depicted in FIG. 3.

A list of reagents is edited in accordance with the flow chart of processing of FIG. 4. In step 4-1, a reagent alarm colored display table and an item counter are initialized. In step 4-2, the item counter is increased by one. In step 4-3, a judgment is made as to whether the item i is requested to be analyzed or not. When the item i is not requested to be analyzed, the situation of the routine goes back to the step 4-2. When the item i is requested to be analyzed, a reagent counter for the item i is initialized in step 4-4. In step 4-5, the reagent counter is increased by one. In step 4-6, a judgment is made as to whether the reagent j is set on the reagent disk or not. When the reagent j is not set on the reagent disk, a red alarm "no reagent" is stored in the column of the item i and the reagent j on the alarm detailed table in step 4-7. When the reagent j is set on the reagent disk, a judgment is made in step 4-8 as to whether the setting position is correct or not. When the setting position is not correct, a red alarm "setting position error" is stored in the column of the item i and the reagent j on the alarm detailed table in step 4-9. When the setting position is correct, a judgment is made in step 4-10 as to whether there is any residue or not.

When there is no residue, a red alarm "no residue" is stored in the column of the item i and the reagent j on the alarm detailed table in step 4-11. When there is any residue, a judgment is made in step 4-12 as to whether the number of residual analyses is not larger than the number of analyses for the reagent residue shortage alarm. When the number of residual analyses is not larger than the number of analyses for the reagent residue shortage alarm, a yellow alarm "residue shortage" is stored in the column of the item i and the reagent j on the alarm detailed table in step 4-13. When the number of residual analyses is larger than the number of analyses for the reagent residue shortage alarm, a judgment is made in step 4-14 as to whether the number of days in use of the reagent is larger than the number of days allowed. When the number of days in use of the reagent is larger than the number of days allowed, a yellow alarm "over the number of days allowed" is stored in the column of the item i and the reagent j on the alarm detailed table in step 4-15. When the number of days in use of the reagent is not larger than the number of days allowed, a judgment is made in step 4-16 as to whether the term of validity of the reagent runs out or not. When the term of validity runs out, a yellow alarm "expiration of the term of validity" is stored in the column of the item i and the reagent j on the alarm detailed table in step 4-17. When the term of validity does not run out, a judgment is made in step 4-18 as to whether the amount of the residue of the reagent j satisfies the number of scheduled analyses of the item i in one day or not. When the amount of the residue does not satisfy the number of scheduled analyses of the item i in one day, a purple alarm "smaller than the number of scheduled analyses in one day" is stored in the column of the item i and the reagent j on the alarm detailed table in step 4-19. When the amount of the residue satisfies the number of scheduled analyses of the item i in one day, the situation of the routine goes to step 4-20. Also after the step 4-7, after the step 4-9, after the step 4-11, after the step 4-13, after the step 4-15, after the step 4-17 or after the step 4-19, the situation of the routine goes to the step 4-20. In the step 4-20, a judgment is made as to whether an alarm having a higher priority than the alarm of the reagent j is set or not in the item i on the alarm colored display table. When the alarm of the reagent j has a higher priority, the alarm color of the reagent j is set in the item i on the alarm colored display table in step 4-21. When the alarm of the reagent j has a lower priority, a judgment is made in step 4-22 as to whether the reagent counter is terminated or not, that is, j reaches the number of reagents for one item or not. When the reagent counter is not terminated, the situation of the routine goes back to the step 4-5. When the reagent counter is terminated, a judgment is made in step 4-23 as to whether the item counter is terminated or not, that is, i reaches the number of items or not. When the item counter is not terminated, the situation of the routine goes back to the step 4-2. When the item counter is terminated, this routine is finished in step 4-24.

Figure 5:
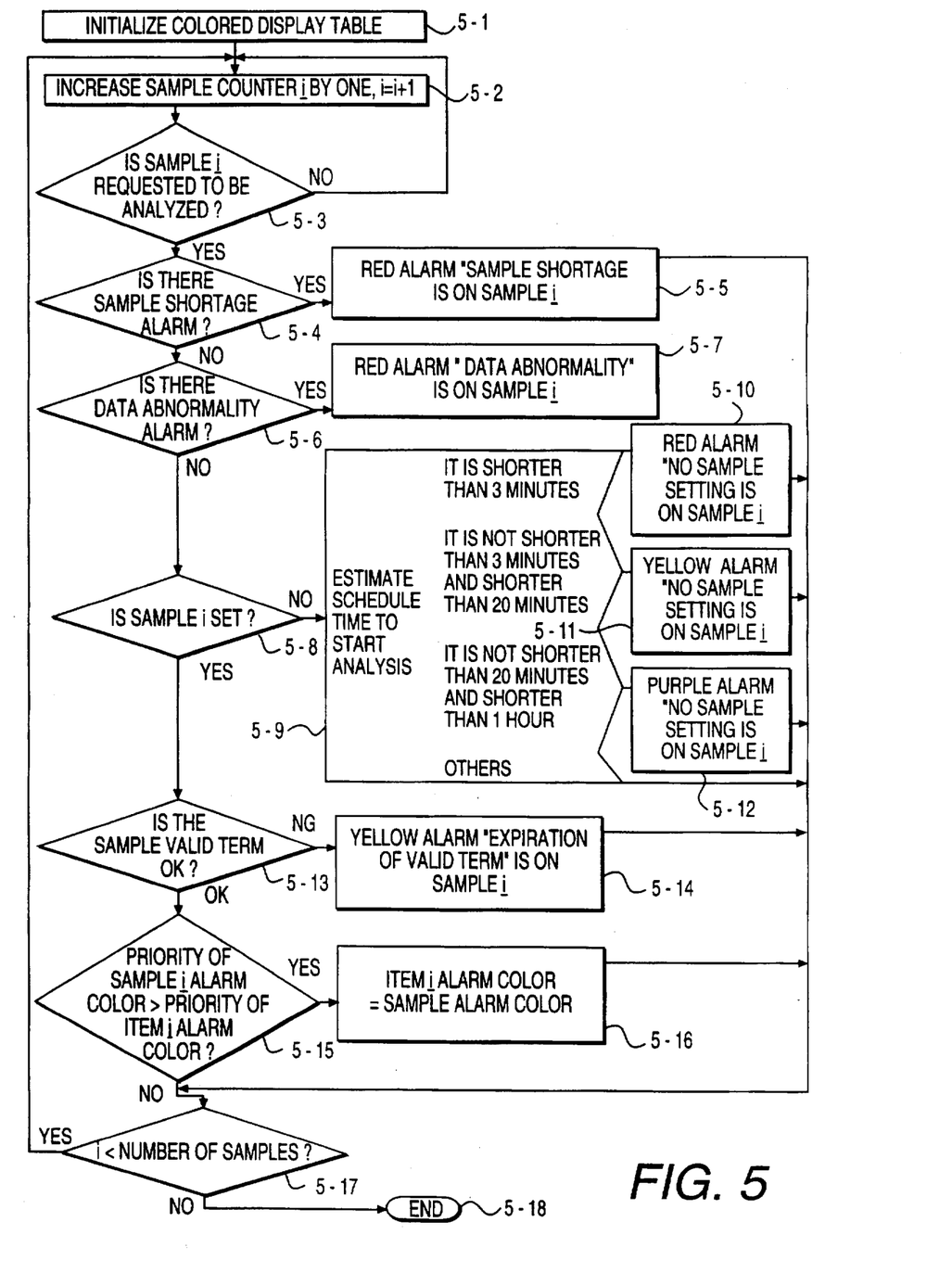
FIG. 5 is a flow chart of the detailed operation showing part of the operation flow depicted in FIG. 3.

As the edition of alarm information concerning standard solutions and control analytes, the routine shown in FIG. 5 is subjected to standard solutions and control analytes, respectively. The "sample" shown in FIG. 5 means a standard solution or control analyte. If a standard solution is under processing, the "sample" means the standard solution. If a control analyte is under processing, the "sample" means the control analyte. In step 5-1, the item alarm of a corresponding sample in the alarm colored display table and a sample counter i are initialized. In step 5-2, the sample counter i is increased by one. In step 5-3, a judgment is made as to whether the sample i is requested to be analyzed or not. When the sample i is not requested to be analyzed, the situation of the routine goes back to the step 5-2. When the sample i is requested to be analyzed, a judgment is made in step 5-4 as to whether a sample shortage alarm occurs or not. When the alarm occurs, a red alarm "sample shortage" is stored in the sample i on the alarm detailed table in step 5-5. When the sample shortage alarm does not occur (inclusive of the case of no data before analysis), a judgment is made in step 5-6 as to whether a data abnormality alarm occurs or not. When the alarm occurs, a red alarm "data abnormality" is stored in the sample i on the alarm detailed table in step 5-7. When the data abnormality alarm does not occur (inclusive of the case of no data before analysis), a judgment is made in step 5-8 as to whether the sample i is set or not. When the sample i is not set, the schedule time up to analysis is estimated in step 5-9. When the schedule time is smaller than 3 minutes, a red alarm "no sample setting" is stored in the sample i on the alarm detailed table in step 5-10. When the schedule time is not smaller than 3 minutes and smaller than 20 minutes, a yellow alarm "no sample setting" is stored in the sample i on the alarm detailed table in step 5-11. When the schedule time is not smaller than 20 minutes and smaller than 1 hour, a purple alarm "no sample setting" is stored in the sample i on the alarm detailed table in step 5-12. When the schedule time is not smaller than 1 hour, no alarm is stored. When the sample i has been set, a judgment is made in step 5-13 as to whether the term of validity runs out or not. When the term of validity runs out, a yellow alarm "expiration of the term of validity" is stored in the sample i on the alarm detailed table in step 5-14. When the term of validity does not run out, the situation of the routine goes to step 5-15. After the step 5-5, after the step 5-7, after the step 5-10, after the step 5-11, after the step 5-12 or after the step 5-14, the situation of the routine goes to the step 5-15.

In the step 5-15, a judgment is made as to whether an alarm having a higher priority than the alarm of the sample i is set in the alarm on the alarm colored display table in each item using the sample i or not. When the alarm of the sample i has a higher priority, the alarm color of the sample i is set in a corresponding item on the alarm colored display table in step 5-16. The situation of the routine goes to step 5-17. In the step 5-17, a judgment is made as to whether the sample counter is terminated or not, that is, i reaches the number of samples or not. When the sample counter is not terminated, the situation of the routine goes back to the step 5-2. When the sample counter is terminated, this routine is finished in step 5-18.

The flow chart of the routine of editing the lists in the step 3-6 of FIG. 3 has been described with reference to FIGS. 4 and 5.

Step 3-7: The contents edited by the step 3-6 are displayed as lists. FIG. 1 shows an example of display. The alarm colored display list is generated by reference to the alarm colored display table on the memory and the information such as the setting position, the production number, the residual amount, etc. on the memory, so that items in which red alarms have occurred are displayed in first priority. Then, items in which yellow alarms have occurred and items in which purple alarms have occurred are displayed in order. The alarm detailed list is generated so that red alarms, yellow alarms and purple alarms are displayed in order with respect to reagents, standard solutions and control analytes.

Step 3-8: If necessary, the lists are printed. If not necessary, the situation of the routine goes to step 3-9. The user judges whether printing is necessary or not.

Figure 6:
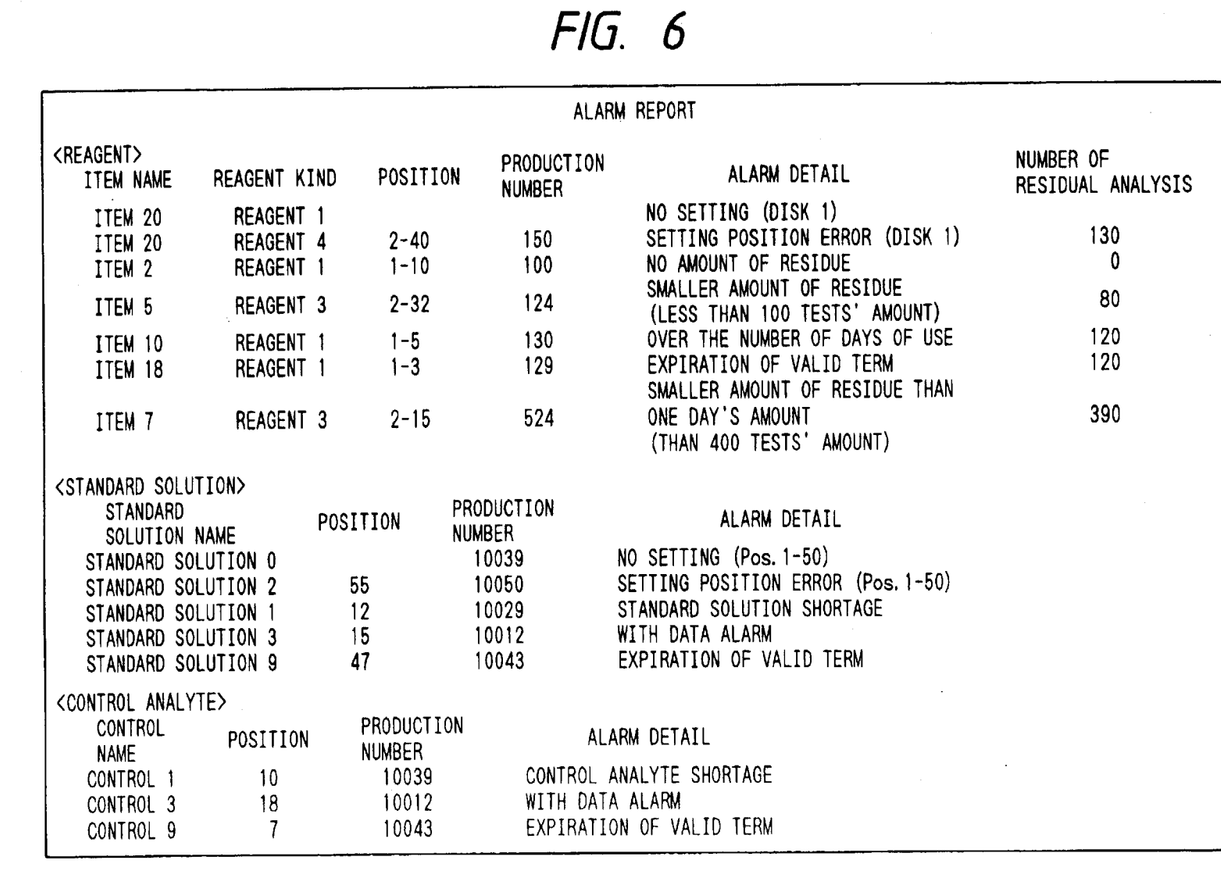
FIG. 6 is a view showing an example of a report printed according to an embodiment of the present invention.

FIG. 6 shows an example of printing. As a report, the setting positions of reagents, standard solutions and control analytes and the same contents as those of the alarm detailed list (alarm detailed table 1-2 in the right of the example of display in FIG. 1) are printed.

Step 3-9: The user takes measures to counter the alarms by reference to the contents displayed by the step 3-7 or the contents printed by the step 3-8. For example, in the case of "reagent shortage", "sample shortage" or "no sample setting", the user does the work of bringing samples from a refrigerator, or the like, to supplement the samples by reference to the report printed by the step 3-8.

After the countermeasures, the situation of the routine automatically goes back to the step 3-2 and the procedure up to the step 3-7 is carried out so that lists are displayed again. The procedure of from the step 3-2 to the step 3-9 is repeated until the alarm countermeasures are taken sufficiently. Alarm display before analysis has been described.

Step 3-10: The procedure surrounded by the broken line in FIG. 3 is an analyzing procedure. When a request to start analysis is inputted through the operation panel, the analysis is started. Samples such as patient analytes, standard solutions, control analytes, etc. are distributed on the basis of the analyzing request of the step 3-5. At the same time, the amounts of residues are detected by the nozzles of the sample distributing mechanisms, so that the amounts of sample residues to be stored in the memory of the micro-computer are updated.

Step 3-11: Reagents necessary for analyzing samples are distributed. At the same time, the amounts of residues are detected by the nozzles of the reagent distributing mechanisms, so that the amounts of sample residues to be stored in the memory of the micro-computer are updated.

Step 3-12: The absorbance of reaction solutions reacted on the reaction disk is measured by the multi-wavelength photometer.

Step 3-13: Analytic result data measured by the step 3-12 are calculated and outputted so as to be stored in the hard disk.

Step 3-14: The lists are edited again on the basis of the amounts of residual samples updated by the step 3-10, the amounts of residual reagents updated by the step 3-11, the data outputted by the step 3-12, the re-judgment of the schedule time of analysis, etc. The editing procedure is the same as that of the step 3-6.

Step 3-15: The alarm list edited by the step 3-14 is displayed in the same manner as the step 3-7.

Step 3-16: If necessary, the list is printed in the same manner as the step 3-8.

Step 3-17: Measures to counter the alarms are taken in the same manner as the step 3-9.

Step 3-18: A judgment is made as to whether all the analyses are finished or not. When all the analyses required are finished, the situation of the routine goes back to the step 3-2. When all the analyses are not finished, the situation of the routine goes back to the step 3-10.

In the aforementioned flow chart of processing, the alarm state is real-time monitored.

According to the preferred embodiments of the present invention, the abnormalities of samples and reagents are detected and the abnormalities thus detected are displayed in the form of a list with the reagent abnormalities associated with the analytic items. Accordingly, measures against abnormalities can be taken speedily.

Further, the abnormalities of samples and reagents in a predetermined time are predictively detected and the abnormalities thus detected are displayed in the form of a list with the reagent abnormalities associated with the analytic items. Accordingly, not only saving of reagents is attained but also lowering of analytic accuracy caused by the abnormalities is lightened.

Since it is obvious that many changes and modifications can be made in the above described details without departing from the nature and spirit of the present invention, it is to be understood that the present invention is not to be limited to the details described herein.

What is claimed is:

1. An automatic analyzer comprising means for reacting samples with reagents so as to obtain reacted solutions, means for measuring the reacted solutions so as to analyze analytic items in the samples, means for detecting possible different abnormalities of each of the reagents, and means for displaying the abnormalities in a ranked list form for each reagent with the abnormalities associated with the analytic items.

2. An automatic analyzer according to claim 1, wherein the displaying means displays the abnormalities with the abnormalities ranked on the basis of a predetermined standard.

3. An automatic analyzer according to claim 2, wherein the predetermined standard is based on a degree of significance of the abnormalities.

4. An automatic analyzer according to claim 2, wherein the predetermined standard is based on a degree of emergence for measures against the abnormalities.

5. An automatic analyzer according to claim 2, wherein the displaying means displays the ranked abnormalities with the abnormalities differently colored.

6. An automatic analyzer according to claim 2, wherein the displaying means displaying abnormalities in the order ranked.

7. An automatic analyzer comprising means for reacting samples with reagents so as to obtain reacted solutions, means for measuring the reacted solutions so as to analyze analytic items in the samples, means for detecting possible different abnormalities of each of the samples and each of the reagents, and means for displaying the abnormalities in a ranked list form, said list form comprising a schematic list indicating relationships between the detected abnormalities and the analytic items for the samples and the reagents, and a detailed list indicating details of the abnormalities corresponding to the relationships between the abnormalities and the analytic items for the samples and the reagents.

8. An automatic analyzer comprising means for reacting samples with reagents so as to obtain reacted solutions, means for measuring the reacted solutions so as to analyze analytic items in the samples, means for predictively detecting possible different abnormalities of each of the reagents in a predetermined time, and means for displaying the abnormalities in a ranked list form with the abnormalities associated with the analytic items.

9. An automatic analyzer according to claim 8, wherein the displaying means displays the abnormalities with the abnormalities ranked on the basis of a predetermined standard.

10. An automatic analyzer according to claim 9, wherein the displaying means displays the ranked abnormalities in the order ranked.

11. An automatic analyzer comprising means for reacting samples with reagents so as to obtain reacted solutions, means for measuring the reacted solutions so as to analyze analytic items in the samples, means for predictively detecting possible different abnormalities of each of the samples and each of the reagents in a predetermined time, and means for displaying the abnormalities in a ranked list form with the abnormalities associated with the analytic items, said list form comprising a schematic list indicating relationships between the detected abnormalities and the analytic items for the samples and the reagents, and a detailed list indicating details of the abnormalities corresponding to the relationships between the abnormalities and the analytic items for the samples and the reagents.

12. An automatic analyzer comprising means for reacting standard solutions and control samples with reagents, respectively, so as to obtain reacted solutions, means for measuring absorbance of the reacted solutions so as to analyze analytic items in the standard solutions and the control samples, means for detecting possible different abnormalities of each of the standard solutions, the control samples and the reagents in a predetermined time, and means for displaying the abnormalities in a ranked list form with the abnormalities associated with the analytic items.

13. An automatic analyzer according to claim 12, wherein said list form comprises a schematic list indicating relationships between the detected abnormalities and the analytic items for the standard solutions, the control samples and the reagents, and a detailed list indicating details of the abnormalities corresponding to the relationships between the abnormalities and the analytic items for the standard solutions, the control samples and the reagents.

14. An automatic analyzer according to claim 13, wherein the details of the abnormalities include information concerning kind, setting position, presence or absence, residual amount and allowed time of the reagents.

15. An automatic analyzer according to claim 14, wherein the details of the abnormalities include information concerning name, setting position, presence or absence, residual amount, data failure and allowed time of the standard solutions, the control samples and the reagents.

* * * * *